United States Patent [19]

McClure

[11] Patent Number: 4,512,040

[45] Date of Patent: Apr. 23, 1985

[54] BIFOCAL INTRAOCULAR LENS

[76] Inventor: Hubert L. McClure, 7777 S. Harvard Pl., Tulsa, Okla. 74136

[21] Appl. No.: 502,695

[22] Filed: Jun. 9, 1982

[51] Int. Cl.³ .......................... A61F 1/16; A61F 1/24
[52] U.S. Cl. ......................................... 3/13; 351/161; 351/168
[58] Field of Search ................. 3/13, 1; 351/159, 161, 351/168

[56] References Cited

U.S. PATENT DOCUMENTS

| | | | |
|---|---|---|---|
| 3,598,479 | 8/1971 | Wright et al. | 351/159 |
| 3,996,627 | 12/1976 | Deeg et al. | 3/13 |
| 4,010,496 | 3/1977 | Neefe | 3/13 |
| 4,077,071 | 3/1978 | Freeman | 3/13 |
| 4,079,470 | 3/1978 | Deeg et al. | 3/13 |
| 4,174,156 | 11/1979 | Glorieux | 351/168 |
| 4,253,199 | 3/1981 | Banko | 3/13 |
| 4,300,818 | 11/1981 | Schachar | 351/159 X |

OTHER PUBLICATIONS

"The Kratz Technique for Cataract Extraction with Lens Implant", (Brochure), Cilco, U.S.A., Cilco, Inc., 1616 13th Ave., Huntington, West Va. 25701, 4 pages, Mar. 20, 1981.
Lens Styles from Cilco, (Advertisement Brochure), Cilco, U.S.A., Cilco, Inc., 1616 13th Ave., Huntington, West Va. 25701, 6 pages, (Optiflex Anterior Chamber Lens on p. 2), Oct. 1982.

Primary Examiner—Ronald L. Frinks
Attorney, Agent, or Firm—Head, Johnson & Stevenson

[57] ABSTRACT

A bifocal intraocular lens consisting of an inner and outer transparent wall defining a centrally located refractive chamber, in the line of sight, and in fluid communication with a vertically positioned reservoir chamber, out of the line of sight, wherein vent tubes connect the remote edge of the refractive chamber to the vertically positioned reservoir chamber. Such an intraocular lens is highly responsive to changes in the angle of inclination of sight by rapidly transferring a liquid of predetermined refractive index in and out of the refractive chamber, thus creating the bifocal effect.

3 Claims, 8 Drawing Figures

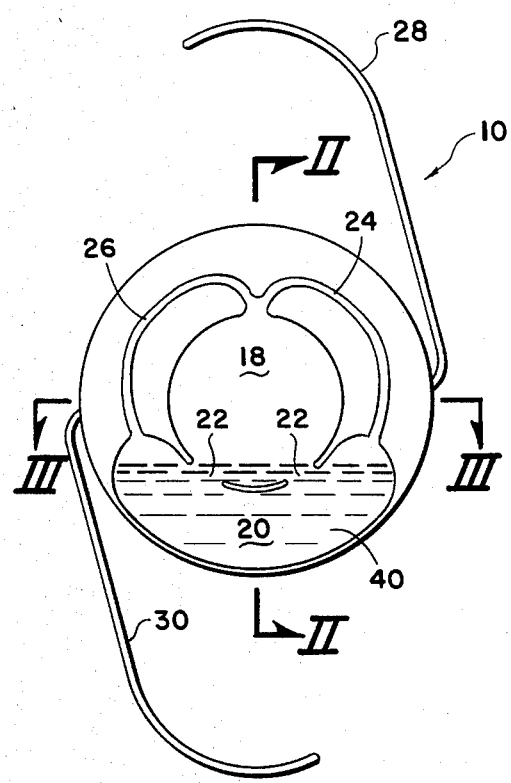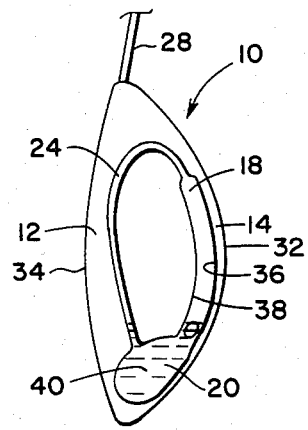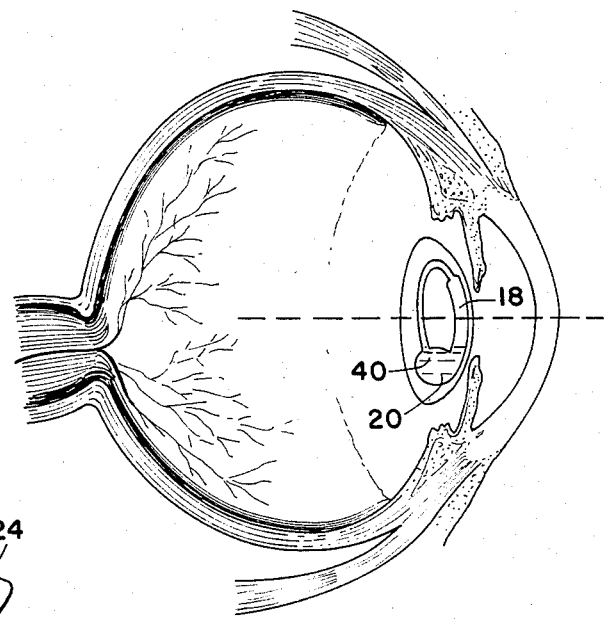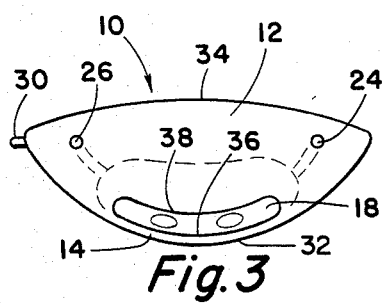
Fig.1
Fig.2
Fig.3
Fig.4

BIFOCAL INTRAOCULAR LENS

BACKGROUND OF THE INVENTION

1. Field of the Invention

This invention relates to an improved intraocular lens adapted for implantation in a human eye. More specifically, the invention relates to a bifocal intraocular lens.

2. Description of the Prior Art

The basic concept of surgically providing a patient with an intraocularly implantable lens as a substitute for the human crystalline lens is generally known. Historically, such lenses have predominatly been made from a high molecular weight polymer such as polymethylmethacrylate. However, U.S. Pat. No. 3,996,627 proposes the use of certain selected glass compositions, while U.S. Pat. No. 4,079,470 discloses the use of low density natural and synthetic crystal such as carborundum, sapphire, ruby, zironium, strontium titanate, diamond and anatase. Various alternative methods and means of attaching the intraocular lens to the eye have been suggested and employed, including posterior chamber implantation, anterior chamber implantation as well as iris fixed intraocular lens. Several specific problems associated with the use of intraocular lens have been addressed in patent literature and elsewhere with varying degrees of success. For example, both U.S. Pat. Nos. 4,010,496 and 4,077,071 disclose the use of either an air space or attachment means of lower density to create a ballast effect or achieve neutral buoyancy. U.S. Pat. No. 4,010,496 also proposes the use of Fresnsel optics with a lens demarcation line positioned such that as the pupil changes from the dilated state to the constricted state a bifocal effect is created. Unfortunately, such a structure allows for close vision only in relatively shaded light and exclusively far vision in bright light.

In U.S. Pat. No. 4,174,156 an optical lens for differential correction comprising two transparent walls defining an enclosed space having therein a quantity of transparent liquid with predetermined optical index is disclosed. In this lens, the bifocal effect is achieved by virtue of the liquid moving in and out of the line of sight in response to the tilting of the eye up and down, thus changing the power of the lens. However, as originally presented in U.S. Pat. No. 4,174,156, this lens is intended to be a contact lens or eyeglass lens and no method of achieving the desired bifocal effect within the physical confines of an intraocular lens is disclosed.

SUMMARY OF THE INVENTION

In view of the prior art and the problems associated with achieving a bifocal effect in an intraocular lens, I have discovered an improved intraocular lens wherein the changing of the power of the lens is achieved by the rapid transfer of a fluid between two chambers within the lens wherein the two chambers are also interconnected by a circumferential vent tube within the lens. Thus, the present invention provides an intraocular lens for implantation into a human eye comprising:

(a) an optical lens suitable for replacing a human crystalline lens wherein the optical lens consists of an inner transparent wall and an outer transparent wall which define an internal closed space within the lens wherein the internal closed space comprises:

(i) a refractive chamber centrally located in the lens such that it is in the line of sight when the lens is implanted into an eye;

(ii) a reservoir chamber in direct fluid communication with the refractive chamber and located in the lens such that it is in vertical alignment with the refractive chamber when the lens is implanted into an eye but not in the line of sight; and (iii) at least one vent tube means within the lens and not in the line of sight wherein the vent tube means establishes fluid communication between the reservoir chamber and the far edge of the refractive chamber remote to the reservoir chamber;

(b) an eye attachment means operatively connected to the optical lens and adapted to fasten and retain the optical lens when implanted into the eye; and (c) a sufficient quantity of a transparent liquid means of predetermined refractive index to partially fill the internally closed space and flow between the refractive chamber and reservoir chamber, in and out of the line of sight, as the angle of inclination of the line of sight changes.

In one embodiment of the invention, the reservoir chamber is below the refractive chamber and the vent tube is a pair of fluid conduits leading from the top edge of the refractive chamber to the respective sides of the lower reservoir chamber. In another embodiment of the invention, the reservoir chamber is above the refractive chamber and the vent tube is a pair of fluid conduits leading from the lower edge of the refractive chamber to each respective side of the upper reservoir chamber.

It is an object of the present invention to provide a bifocal intraocular lens which changes focal length according to the angle of inclination of the eye by the transfer of a fluid of predetermined refractive index. It is another object of the present invention to provide a means within the intraocular lens which will insure the rapid transfer of the refractive fluid in and out of the line of sight. Fulfillment of these objects and the presence and fulfillment of additional objects will be apparent upon complete reading of the specification and claims, taken in conjunction with the attached drawings.

BRIEF DESCRIPTION OF THE DRAWINGS

FIG. 1 illustrates an intraocular lens according to the present invention wherein the liquid reservoir is located below the refractive chamber.

FIG. 2 is a cross-sectional side view of the intraocular lens of FIG. 1.

FIG. 3 is a cross-sectional top view of the intraocular lens of FIG. 1.

FIGS. 4 and 5 are simplified cross-sectional views of an eye with an implanted intraocular lens according to the present invention illustrating how it functions.

DESCRIPTION OF THE PREFERRED EMBODIMENTS

Figure 6:
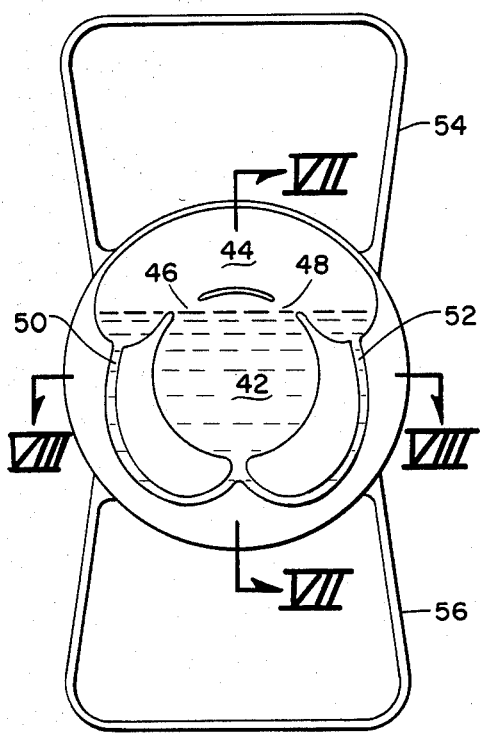
FIG. 6 illustrates an intraocular lens according to the present invention wherein the air reservoir is located over the refractive chamber.

The bifocal intraocular lens according to the present invention, how it functions, and how it differs from what has been previously employed can perhaps be best explained and understood by reference to the drawings. FIG. 1 illustrates the front view of one preferred embodiment of an intraocular lens according to the present invention, generally designated by the numeral 10. FIGS. 2 and 3 are a side and top cross-sectional view of the intraocular lens 10 as seen through lines II—II, and III—III, respectively. As seen in FIGS. 2 and 3, the intraocular lens 10 is made up of an inner transparent wall 12 and an outer transparent wall 14 which define an internally closed space within the lens 10. As further illustrated, this internally closed space comprises a centrally located refractive chamber 18 positioned above a liquid filled reservoir chamber 20. Refractive chamber 18 and reservoir chamber 20 are directly interconnected vertically by passages 22. Also, the upper edge of the refractive chamber 18 is connected to each side of the lower reservoir chamber 20 by a pair of vent tubes 24 and 26 which circumvent the refractive chamber 18 and the line of sight as explained later. Vent tubes 24 and 26 are positioned within the lens 10 such that they are horizontally displaced away from the refractive chamber 18.

As further illustrated in FIG. 1, the outer perimeter of the transparent walls are equipped, in this embodiment, with a pair of J-loop posterior attachment means 28 and 30. It should be appreciated that the improved intraocular lens of the present invention can be employed with essentially any contemporary eye fastening mechanism or method. Thus, it is contemplated that the intraocular lens can be used in conjunction with any appropriate anterior or posterior fastening means or medium as well as being attached to the iris by any of the methods well known in the art, and as such, geometric configurations, designs and structures other than the J-hook or J-loop should be considered equivalent for purposes of this invention.

The intraocular lens 10 is intended to be surgically implanted into the human eye as a substitute for the natural crystalline lens. During implantation the refractive chamber 18 is aligned in the line of sight such that the light entering the eye passes through the central portion of the lens 10. The central portion of the lens 10 consists of the lenticular portion of the intraocular lens and as such, has an appropriate optical grade anterior and posterior refractive surface 32 and 34. In addition, the central lenticular portion of the intraocular lens contains the refractive chamber 18 inside the lens. This refractive chamber is essentially a hollow area with two additional optical grade refractive surfaces within the lens itself, an inner anterior and posterior surface 36 and 38.

Figure 5:
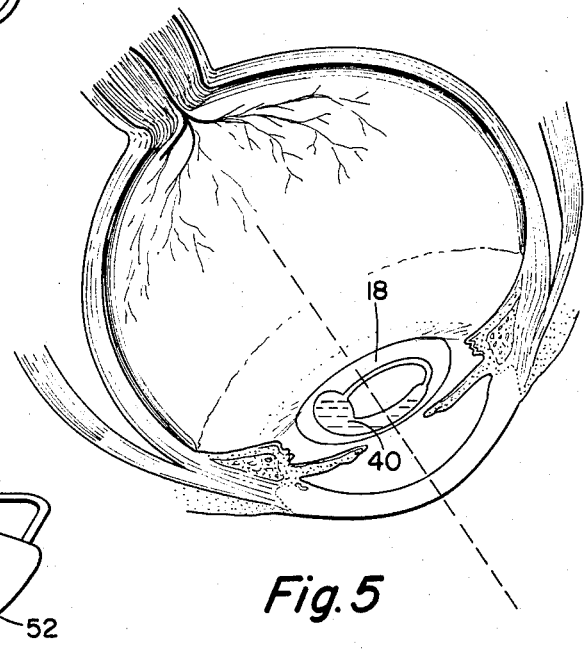

It is the combination of these four refractive surfaces that establishes the refractive prescription of the lens. Furthermore, and as illustrated in FIGS. 4 and 5, the liquid reservoir 20 is filled, for far vision, with a liquid of predetermined refracrive index, while the refractive chamber 18 is filled with air or other inert vapor. Thus, the volumes of the respective chambers 18 and 20 and liquid 40 are selected such that when the lens is in a vertical configuration associated with horizontal view, the liquid remains entirely within the lower reservoir 20. As the angle of inclination of the line of sight tilts downward, the liquid previously in the lower chamber 20 flows into the refractive chamber 18 and in a similar manner, as the eye position returns to the horizontal sight, the liquid in the refractive chamber 18 drains back to the lower reservoir chamber 20. In this manner, the refractive prescription of the lens will change by virtue of the presence or absence of the liquid in the line of sight (i.e., a liquid filled or empty refractive chamber 18). By preselecting the refractive index of the liquid and controlling the geometric contours and relative positions of the refractive surfaces, the intraocular lens can be tailored to the specific needs of the patient.

In order to achieve the desired beneficial effects of the transfer of a refractive liquid in and out of the line of sight within the small geometric confines of an intraocular lens, it has been discovered that there must be connecting vent tubes between the refractive chamber and the reservoir. These vent tubes must be positioned such as to provide for rapid transfer of liquid in and out of the line of sight. In order to achieve this, the vertical tubes represent and can be envisioned as being the final element that completes a circular loop or pathway for fluid flow. As the liquid phase exits one chamber and enters the other chamber, the vent tubes are positioned such that the gaseous phase within the chamber being filled can be displaced through the vent tube back to the chamber that is emptying. This cyclic fluid pathway thus prevents localized vapor pockets that tend to resist the desired rapid liquid transfer from chamber to chamber. Preferably, and as illustrated in the drawings, the vent tubes circumvent the central refractive chamber in a plane that is displaced horizontally from the refractive chamber. In this manner, the vent tubes assume a position displaced vertically over the chamber as the line of sight tilts downward. Again, this feature insures the circulation of the gaseous phase through the vent tubes and as such, represents an aspect of the invention which could not be readily achieved in the previous differential contact lens of U.S. Pat. No. 4,174,156. In other words, because of the lenticular nature of the intraocular lens, the incorporation of vent tubes to complete a cyclic flow pathway to assist rapid liquid transfer is achieved.

Further, because of the lenticular of the intraocular lens, the reservoir chamber which is located inferiorly relative to the refractive chamber can advantageously be located posteriorly to the refractive chamber as illustrated in FIG. 2. Because of this posterior relationship, the sensitivity of the fluid transfer from the reservoir chamber into the line of sight as a function of the motion of the eye turning downward is enhanced, thus again, insuring more rapid and abrupt change from a distant focal length to close vision. Consequently, the intraocular lens of the present invention becomes a far more acceptable bifocal lens with a more rapid and more quickly induced transition between optical focal length options.

Figure 7:
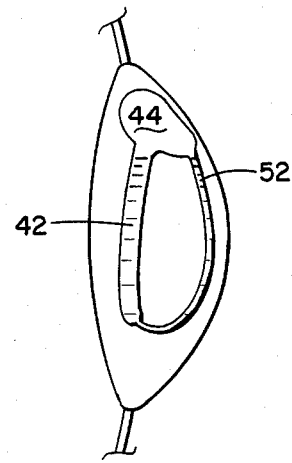
FIG. 7 is a side view of the intraocular lens of FIG. 6.
Figure 8:
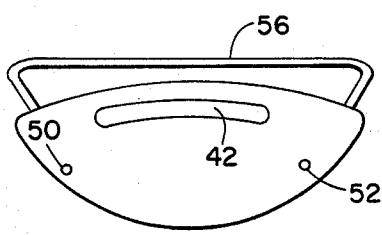
FIG. 8 is a top view of the intraocular lens of FIG. 6.

FIGS. 6, 7 and 8 illustrate an alternate preferred embodiment wherein the centrally located refractive chamber 42 is normally filled with the liquid when the line of sight is essentially horizontal and the reservoir chamber 44 is located directly above the refractive chamber 42. Again, the refractive chamber 42 and the reservoir chamber 44 are in direct fluid communication with each other by virtue of passages 46 and 48 and the lower edge of the refractive chamber 42 is connected to each side of the upper reservoir chamber 44 by a pair of vent tubes 50 and 52 which circumbent the refractive chamber 42 in the line of sight in a manner analogous to the previous preferred embodiment. The vent tubes 50 and 52 are again positioned within the lens such that they are horizontally displaced away from the refractive chamber 42. A pair of anterior attachment loops 54 and 56 are mounted to the outer edge of the lens.

The embodiment illustrated in FIGS. 6 through 8 performs in a manner somewhat analogous to that of the previous embodiment of FIGS. 1 through 3, except the upper reservoir chamber 44 in this embodiment is filled, for far vision, with air or other suitable inert vapor and the refractive chamber 42 is filled with a liquid. As stated above, when the line of sight is essentially horizontal, the refractive chamber is filled with liquid. As the eye is turned downward, the liquid drains from the refractive chamber 42 into the reservoir chamber 44. Preferably, and as illustrated, the reservoir chamber 44 is anteriorly displaced relative to the refractive chamber 42, thus taking advantage of the lenticular nature of the intraocular lens to enhance the sensitivity of the fluid transfer from one chamber to the next. Also, it should be appreciated that the vent tubes 50 and 52 in this embodiment actually provide for the delivery of the liquid phase as opposed to a transfer of the gaseous phase in the other alternate embodiment.

It is contemplated that the intraocular lens of the present invention can be manufactured out of any of the compositions known in the art and, as previously stated, implanted and fastened to the eye by any of the conventional methods and equipment. The actual construction of the lens will involve the precision manufacturing of two separate half lenses which are assembled into a single intraocular lens with the cavity between the halves subsequently being partially filled with the liquid and then sealed. In addition, the previously mentioned advantages associated with the rapid transfer of liquid in and out of the line of sight and resulting bifocal option, the intraocular lens of the present invention is further contemplated as being readily amenable to achieving neutral buoyancy by virtue of the presence of the partially filled internal space in the lens.

Having thus described and exemplified the preferred embodiments with a certain degree of particularity, it is manifest that many changes can be made within the details of the invention without departing from the spirit and scope of this invention. Therefore, it is to be understood that the invention is not limited to the embodiments set forth herein for purposes of exemplification, but is to be limited only by the scope of the attached claims, including the full range of equivalents to which each element thereof is entitled.

I claim:
1. An intraocular lens for implantation into a human eye comprising:
(a) an optical lens suitable for replacing a human crystalline lens wherein said optical lens consists of an inner transparent wall and an outer transparent wall which define an internal closed space within said lens wherein said internal closed space comprises:
  (i) a refractive chamber centrally located in said lens such that it is in the line of sight when said lens is implanted into an eye;
  (ii) a reservoir chamber in direct fluid communication with said refractive chamber and located in said lens such that it is in vertical alignment with said refractive chamber when said lens is implanted into an eye but not in the line of sight; and
  (iii) at least one vent tube means within said lens and not in the line of sight wherein said vent tube means establishes fluid communication between said reservoir chamber and the far edge of said refractive chamber remote to said reservoir chamber;
(b) an eye attachment means operatively connected to said optical lens and adapted to fasten and retain said optical lens when implanted into the eye; and
(c) a sufficient quantity of a transparent liquid means of predetermined refractive index to partially fill said internally closed space and flow between said refractive chamber and reservoir chamber, in and out of the line of sight, as the angle of inclination of the line of sight changes.

2. An intraocular lens of claim 1 wherein said reservoir chamber is below said refractive chamber and said vent tube means is a pair of fluid conduits leading from the top edge of said refractive chamber to each respective side of the lower reservoir chamber.

3. An intraocular lens of claim 1 wherein said reservoir chamber is above said refractive chamber and said vent tube means is a pair of fluid conduits leading from the lower edge of said refractive chamber to each respective side of the upper reservoir chamber.

* * * * *